United States Patent
Dodge et al.

(10) Patent No.: US 6,723,739 B1
(45) Date of Patent: Apr. 20, 2004

(54) GLUCOPYRANOSIDE BENZOTHIOPHENES

(75) Inventors: Jeffrey A. Dodge, Indianapolis, IN (US); Charles A. Frolik, Indianapolis, IN (US); Terry D. Lindstrom, Indianapolis, IN (US); Charles W. Lugar, III, McCordsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 1,647 days.

(21) Appl. No.: 08/405,555

(22) Filed: Mar. 15, 1995

Related U.S. Application Data

(62) Division of application No. 08/246,655, filed on May 20, 1994, now abandoned.

(51) Int. Cl.[7] .................. A61K 31/351; A61K 31/381; A61K 31/4453; A61K 31/44
(52) U.S. Cl. ................ 514/324; 514/326; 514/337
(58) Field of Search ................ 514/324, 326, 514/337

(56) References Cited

U.S. PATENT DOCUMENTS

| | | | |
|---|---|---|---|
| 4,418,068 A | 11/1983 | Jones | 424/267 |
| 5,393,763 A | * 2/1995 | Black et al. | 514/333 |

FOREIGN PATENT DOCUMENTS

| | | |
|---|---|---|
| EP | 584952 | 3/1994 |

OTHER PUBLICATIONS

Frolik et al, "In Vivo and In Vitro Metabolism of Raloxifene" Am. Soc. Bone & Min. Res., Tampa, Sep. 18–22, 1993.

Lindstrom et al "Disposition and Metabolism of New Benzthiophene Antiestrogin in Rats, Dogs, Monkeys," *Xenobiotica*, 14(*11*), 841–847 (1984).

Black et al., "The Relationship of the Antiestrogenic Efficacy of LY156758 to its Pharmacokinetics and Metabolism following Oral Administration to Adult Ovariectomized Rats", 7th Int'l Congress of Endrocrin, Quebec City Jul. 1–7, 1984, ABS 323.

Lantz et al., "HPLC Determination of Raloxifene Before and After Hydrolysis of Human Plasma", AAPS, Orlando FL, Nov. 14–18, 1993.

* cited by examiner

*Primary Examiner*—Ba K. Trinh
(74) *Attorney, Agent, or Firm*—William R. Boudreaux; James J. Sales

(57) ABSTRACT

A compound of the formula

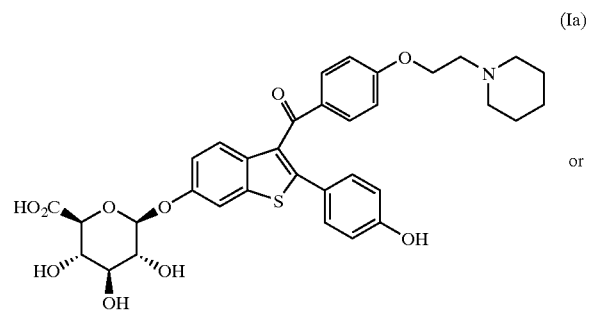

(Ia)

or

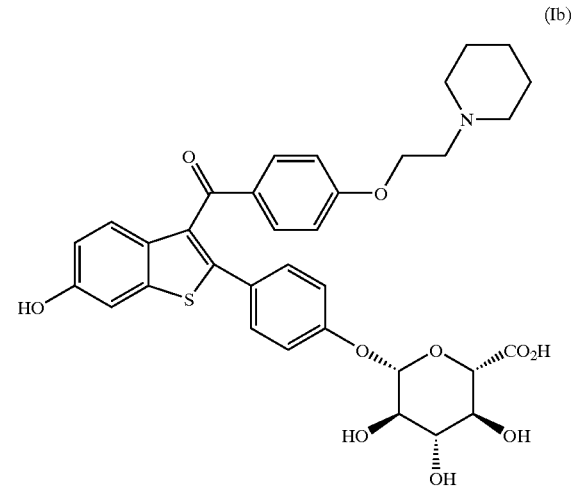

(Ib)

or a pharmaceutically acceptable salt or solvate thereof. Also provided by the invention are methods of use of the above compounds, and processes for the preparation thereof.

1 Claim, No Drawings

GLUCOPYRANOSIDE BENZOTHIOPHENES

This application is a continuation, division, of application Ser. No. 08/246,655, filed May 20, 1994 now abandoned.

FIELD OF THE INVENTION

The invention relates to benzothiophenes glucuronidated at either the 4' or 6 position, and processes for preparation and uses thereof.

BACKGROUND OF THE INVENTION

The current major diseases or conditions of bone which are of public concern include post-menopausal osteoporosis, senile osteoporosis, patients undergoing long-term treatment of corticosteroids, side effects from glucocorticoid or steroid treatment, patients suffering from Cushings's syndrome, gonadal dysgensis, periarticular erosions in rheumatoid arthritis, osteoarthritis, Paget's disease, osteohalisteresis, osteomalacia, hypercalcemia of malignancy, osteopenia due to bone metastases, periodontal disease, and hyperparathyroidism. All of these conditions are characterized by bone loss, resulting from an imbalance between the degradation of bone (bone resorption) and the formation of new healthy bone. This turnover of bone continues normally throughout life and is the mechanism by which bone regenerates.

However, the conditions stated above will tip the balance towards bone loss such that the amount of bone resorbed is inadequately replaced with new bone, resulting in net bone loss.

One of the most common bone disorders is post-menopausal osteoporosis which affects an estimated 20 to 25 million women in the United States alone. Women after menopause experience an increase in the rate of bone turnover with resulting net loss of bone, as circulating estrogen levels decrease. The rate of bone turnover differs between bones and is highest in sites enriched with trabecular bone, such as the vertebrae and the femoral head. The potential for bone loss at these sites immediately following menopause is 4–5% per year. The resulting decrease in bone mass and enlargement of bone spaces leads to increased fracture risk, as the mechanical integrity of bone deteriorates rapidly.

At present, there are 20 million people with detectable vertebral fractures due to osteoporosis and 250,000 hip fractures per year attributable to osteoporosis in the U.S. The latter case is associated with a 12% mortality rate within the first two years and 30% of the patients will require nursing home care after the fracture. Therefore, bone disorders are characterized by a noticeable mortality rate, a considerable decrease in the survivor's quality of life, and a significant financial burden to families.

Essentially all of the conditions listed above would benefit from treatment with agents which inhibit bone resorption. Bone resorption proceeds by the activity of specialized cells called osteoclasts. Osteoclasts are unique in their ability to resorb both the hydroxyapatite mineral and organic matrix of bone. They are similar to the cartilage resorbing cells, termed chondroclasts. It is for this reason that potent inhibitors of osteoclastic bone resorption may also inhibit the cell-mediated degradation of cartilage observed in rheumatoid arthritis and osteoarthritis.

Therapeutic treatments to impede net bone loss include the use of estrogens. Estrogens have been shown clearly to arrest the bone loss observed after menopause and limit the progression of osteoporosis; but patient compliance has been poor because of estrogen side-effects. These side effects include resumption of menses, mastodynia, increase in the risk of uterine cancer, and possibly an increase in the risk of breast cancer.

Alternatively, calcitonin has been used to treat osteoporotic patients. Salmon calcitonin has been shown to directly inhibit the resorption activity of mammalian osteoclasts and is widely prescribed in Italy and Japan. However, calcitonins are prohibitively expensive to many and appear to be short-lived in efficacy. That is, osteoclasts are able to "escape" calcitonin inhibition of resorption by down-regulating calcitonin receptors. Therefore, recent clinical data suggest that chronic treatment with calcitonin may not have long term effectiveness in arresting the post-menopausal loss of bone.

A compound now in clinical trials for inhibiting bone loss and lowering lipid levels is raloxifene, having the formula

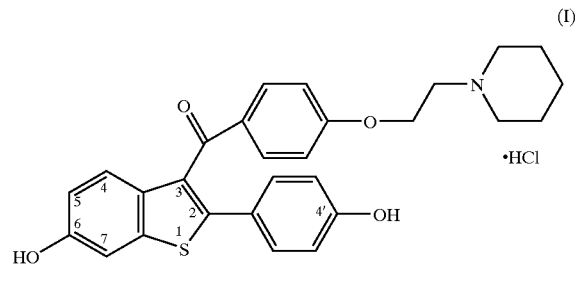

(I)

When raloxifene is administered orally to humans there has been an absence of detectable concentrations of raloxifene in systemic circulation. This is due, in large part, to metabolism of the drug. Unfortunately, the exact human metabolites have not previously been isolated in pure form, and thus the structures not unequivocally established.

The exact structures of two human metabolites have now been identified, including the regiochemistry and the stereochemical integrity (α vs β) of the glycosidic bond.

SUMMARY OF THE INVENTION

The invention encompasses a compound of the formula

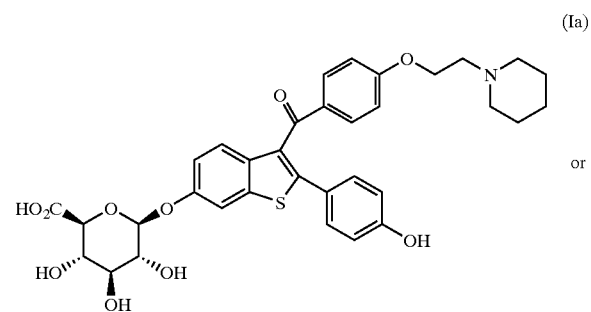

(Ia)

or

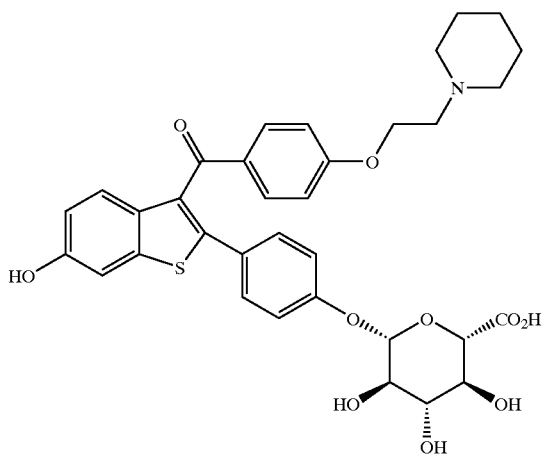

(Ib)

or a pharmaceutically acceptable salt or solvate thereof. Also encompassed by the invention are methods of use of the above, and processes for preparation thereof.

DETAILED DESCRIPTION OF THE INVENTION

The current invention concerns the discovery that compounds of formula I are useful for lowering serum cholesterol levels and inhibiting bone resorption and bone loss. Methods of use are also provided by this invention and are practiced by administering to a human in need thereof a dose of a compound of formula I or a pharmaceutically acceptable salt or solvate thereof to lower serum cholesterol levels, or inhibit bone loss or resorption.

It has been determined that compound Ib is the predominant human metabolite.

The term "inhibit" is defined to include its generally accepted meaning which includes preventing, prohibiting, restraining, and slowing, stopping or reversing progression, or severity, and holding in check and/or treating existing characteristics. The present method includes both medical therapeutic and/or prophylactic treatment, as appropriate.

Generally, the compound is formulated with common excipients, diluents or carriers, and compressed into tablets, or formulated as elixirs or solutions for convenient oral administration, or administered by the intramuscular or intravenous routes. The compounds can be administered transdermally, and are well suited to formulation as sustained release dosage forms and the like.

The methods of the present invention are useful in men, as well as women. Preferably, however, the methods of the present invention are useful in women, more preferably estrogen deficient women.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases useful in the preparation of addition salts include sodium hydroxide, potassium hydroxide, ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, parenteral mixtures and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The dosage of a compound of formula I required to inhibit bone loss or lower serum cholesterol will depend on the severity of the disease, its route of administration, and related factors that will be decided by the attending physician. Generally, a dosage of about 0.1 to 1000 mg/day will be effective.

The compositions are preferably formulated in a unit dosage form, each dosage containing about 0.1 to about 1000 mg. The term "unit dosage form" refers to physically discrete units, such as tablets and capsules, suitable as unitary dosages, particularly as unitary daily dosages, for human subjects and other mammals, each unit containing a predetermined quantity of active material calculated to produce the desired therapeutic effect, in association with a suitable pharmaceutical excipient.

The term or period of time of administration to a human subject will vary depending upon severity of the condition, patient health, and related factors which will be decided upon by the attending physician. A course of treatment is expected to be at least for a period of six months, more normally at least one year, and preferably on a continual basis.

Examples of formulations using the dosage range follow:

Formulations

| Formulation 1: Gelatin Capsules Hard gelatin capsules are prepared using the following: | |
|---|---|
| Ingredient | Quantity (mg/capsule) |
| Compound of formula I | 50–150 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of capsule formulations include those shown below:

| Formulation 2: Compound of Formula I Capsule | |
|---|---|
| Ingredient | Quantity (mg/capsule) |
| Compound of formula I | 60 |
| Starch, NF | 112 |
| Starch flowable powder | 225.3 |
| Silicone fluid 350 centistokes | 1.7 |

| Formulation 3: Compound of Formula I capsule | |
|---|---|
| Ingredient | Quantity (mg/capsule) |
| Compound of formula I | 75 |
| Starch, NF | 108 |
| Starch flowable powder | 225.3 |
| Silicone fluid 350 centistokes | 1.7 |

| Formulation 4: Compound of Formula I capsule | |
|---|---|
| Ingredient | Quantity (mg/capsule) |
| Compound of formula I | 100 |
| Starch, NF | 103 |
| Starch flowable powder | 225.3 |
| Silicone fluid 350 centistokes | 1.7 |

| Formulation 5: Compound of Formula I capsule | |
|---|---|
| Ingredient | Quantity (mg/capsule) |
| Compound of formula I | 125 |
| Starch, NF | 150 |
| Starch flowable powder | 397 |
| Silicone fluid 350 centistokes | 3.0 |

| Formulation 6: Compound of Formula I capsule | |
|---|---|
| Ingredient | Quantity (mg/capsule) |
| Compound of formula I | 150 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

| Formulation 7: Tablets | |
|---|---|
| Ingredient | Quantity (mg/tablet) |
| Compound of formula I | 60 |
| Cellulose, microcrystalline | 0–650 |
| Silicon dioxide, fumed | 0–650 |
| Stearate acid | 0–15 |

| Formulation 8: Tablets | |
|---|---|
| Ingredient | Quantity (mg/tablet) |
| Compound of formula I | 75 |
| Cellulose, microcrystalline | 0–650 |
| Silicon dioxide, fumed | 0–650 |
| Stearate acid | 0–15 |

| Formulation 9: Tablets | |
|---|---|
| Ingredient | Quantity (mg/tablet) |
| Compound of formula I | 100 |
| Cellulose, microcrystalline | 0–650 |

-continued

Formulation 9: Tablets

| Ingredient | Quantity (mg/tablet) |
|---|---|
| Silicon dioxide, fumed | 0–650 |
| Stearate acid | 0–15 |

Formulation 10: Tablets

| Ingredient | Quantity (mg/tablet) |
|---|---|
| Compound of formula I | 125 |
| Cellulose, microcrystalline | 0–650 |
| Silicon dioxide, fumed | 0–650 |
| Stearate acid | 0–15 |

Formulation 11: Tablets

| Ingredient | Quantity (mg/tablet) |
|---|---|
| Compound of formula I | 150 |
| Cellulose, microcrystalline | 0–650 |
| Silicon dioxide, fumed | 0–650 |
| Stearate acid | 0–15 |

The components are blended and compressed to form tablets.

Alternatively, tablets each containing 50 to 150 mg of active ingredient are made up as follows:

Formulation 12: Tablets

| Ingredient | Quantity (mg/tablet) |
|---|---|
| Compound of formula I | 60 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

Formulation 13: Tablets

| Ingredient | Quantity (mg/tablet) |
|---|---|
| Compound of formula I | 75 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

Formulation 14: Tablets

| Ingredient | Quantity (mg/tablet) |
|---|---|
| Compound of formula I | 100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

Formulation 15: Tablets

| Ingredient | Quantity (mg/tablet) |
|---|---|
| Compound of formula I | 125 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

Formulation 16: Tablets

| Ingredient | Quantity (mg/tablet) |
|---|---|
| Compound of formula I | 150 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 50–150 mg of medicament per 5 mL dose are made as follows:

Formulation 17: Suspensions

| Ingredient | Quantity (mg/5 ml) |
|---|---|
| Compound of formula I | 60 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

| Formulation 18: Suspensions | |
|---|---|
| Ingredient | Quantity (mg/5 ml) |
| Compound of formula I | 75 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

| Formulation 19: Suspensions | |
|---|---|
| Ingredient | Quantity (mg/5 ml) |
| Compound of formula I | 100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

| Formulation 20: Suspensions | |
|---|---|
| Ingredient | Quantity (mg/5 ml) |
| Compound of formula I | 125 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

| Formulation 21: Suspensions | |
|---|---|
| Ingredient | Quantity (mg/5 ml) |
| Compound of formula I | 150 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

The compounds needed as starting materials can be made according to established procedures, such as those detailed in U.S. Pat. Nos. 4,133,814, 4,418,068, and 4,380,635, all of which are incorporated by reference herein. In general, the process starts with a benzo[b]thiophene having a 6-hydroxyl group and a 2-(4-hydroxyphenyl) group. The hydroxyl groups of the starting compound are protected, the three position is acylated, and the product deprotected to form the compounds needed for starting material. Examples of the preparation of such compounds are provided in the U.S. patents discussed above.

The starting materials may be manipulated as set out in the Scheme, below.

Scheme

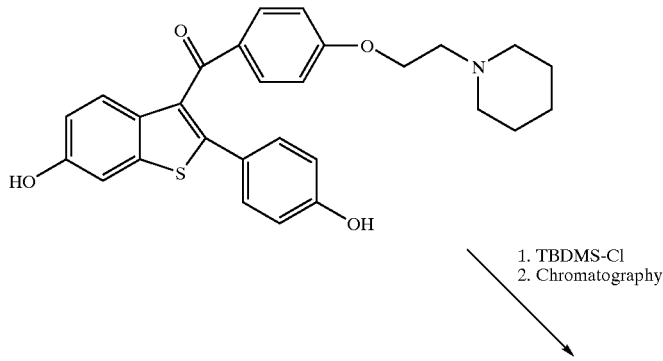

1. TBDMS-Cl
2. Chromatography

-continued

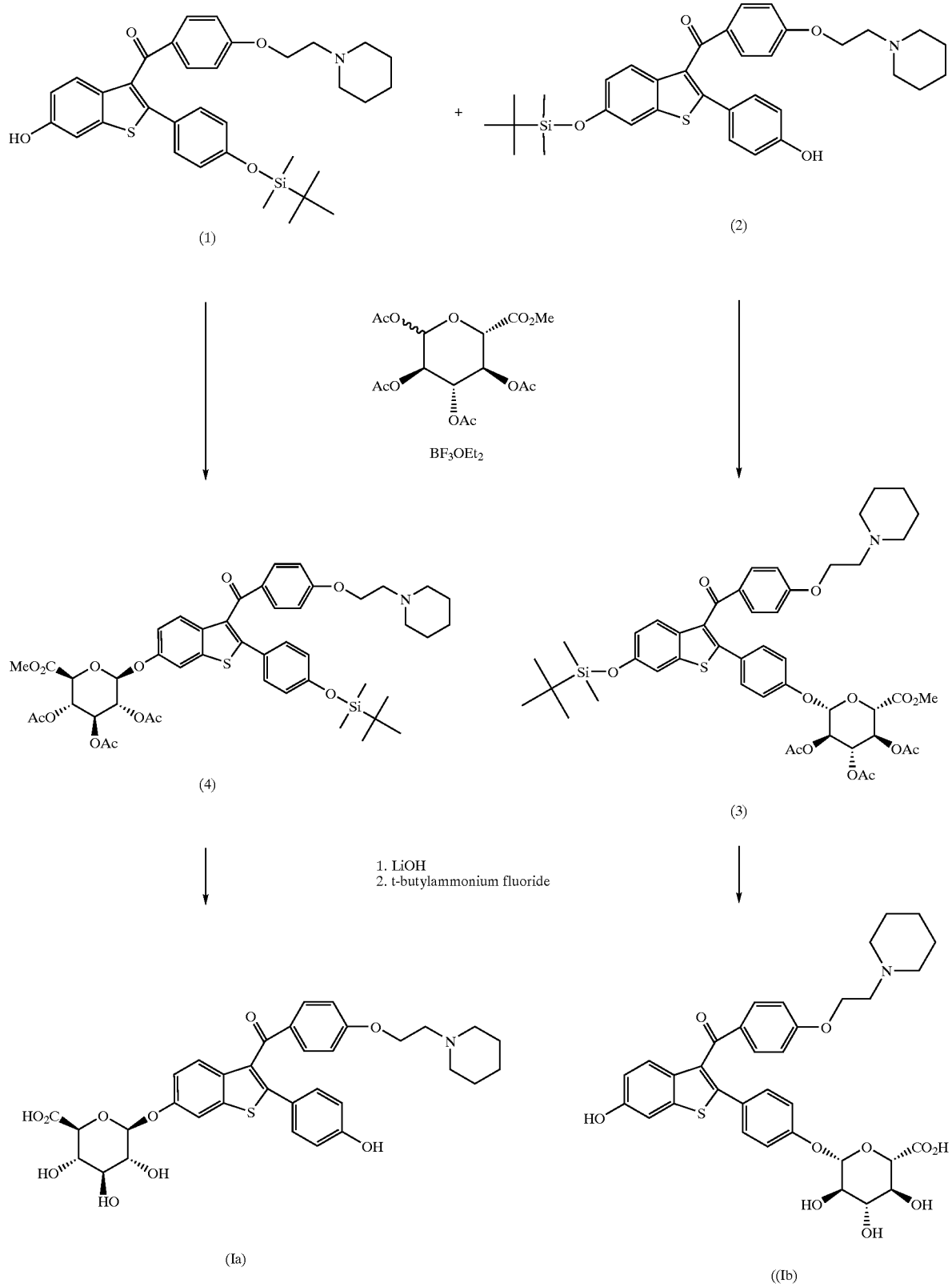

The process in the Scheme is carried out under substantially anhydrous conditions which represents reaction conditions which are virtually free from water. Accordingly, solvents are dried prior to use in the process. Suitable polar organic solvents include methylene chloride, chloroform, methyl alcohol, toluene, and di-or trichloroethane, tetrahydrofuran (THF), dimethylpropylene urea (DMPU), hexamethylphosphoric triamide (HMPA), dimethyl acetamide, tetrahydropyran, dioxane, acetonitrile, diethyl ether, dimethylacetamide, dimethylsulfoxide, dimethoxyethane, and mixtures thereof.

The term "suitable base" refers to primary or secondary amines or an alkali metal hydroxide. Such suitable bases which can be used as nucleophiles include $C_1$–$C_7$ primary and $C_2$–$C_{14}$ secondary amines such as methylamine, ethylamine, propylamine, butylamine, pentylamine, hexylamine, heptylamine, dimethylamine, diethylamine, dipropylamine, dibutylamine, dipentylamine, dihexylamine, diheptyl, methylethylamine, methylpropylamine, methylbutylamine, methylpentylamine, methylhexylamine, methylheptylamine, ethylpropylamine, ethylbutylamine, ethylpentylamine, ethylhexylamine, ethylheptylamine, propylbutylamine propylpentylamine, propylhexylamine, propylheptylamine, benzylamine, and the like. Further examples of secondary amines include tetrahydropyazole, piperidine and the like. Also included are the diamines such as N,N-diethylethylenediamine, and the like.

Preferred "suitable bases" include lithium hydroxide and N,N-diethylethylene diamine.

Terms such as "protected hydroxy" and "hydroxy protecting group", mean hydroxy moieties bonded to conventional groups stable to the reaction conditions in the process aspect of the instant invention. Such groups include the formyl group, the benzhydryl group, the trityl group, the trimethylsilyl group, and the like. Similar hydroxy-protecting groups such as those described by C. B. Reese and E. Haslam in "Protective Groups in Organic Chemistry" J. F. W. McOmie, Ed., Plenum Press, New York, N.Y., 1973, Chapters 3 and 4, and T. W. Greene, "Protective Groups in Organic Synthesis", John Wiley and Sons, New York, N.Y., 1981, Chapter 2 shall be recognized as suitable. All that is further required of these groups is that one skilled in the art is able to substitute and remove them from the hydroxy group(s) without disrupting the remainder of the molecule. The preferred hydroxy protecting group is t-butyldimethylsilyl (TBDMS).

The reactions in the Scheme may be run at temperatures of between about –100° C. to about 80° C., and more preferably from 0 to 25° C.

From the starting materials described previously herein, a hydroxy-protecting group is introduced at either the 4' or 6 position hydroxy, which leaves the other hydroxy group vulnerable to glucuronidation. The single hydroxy-protected compound is then subjected to a Lewis acid, such as boron trifluorate etherate, tin (II) chloride, $ZnCl_3$, and aluminum chloride for example, and the appropriate glucopyranuranate. The glucuronidated compound is then subjected to a suitable base and a reagent to cleave the protecting group, such as tetrabutyl ammonium fluoride.

The following examples illustrate the preparation of the compounds used in the invention.

PREPARATION 1

6-Hydroxy-2-(4-hydroxyphenyl)-3-[4-(2-piperidinoethoxy)benzoyl]benzo[b]thiophene A 4 g. portion of 6-methanesulfonyloxy-2-(4-methanesulfonyloxyphenyl)-3-[4-(2-piperidinoethoxy)-benzoyl]benzo[b]thiophene, hydrochloride, was combined with 100 ml. of denatured alcohol and 10 ml. of 5 N sodium hydroxide, and stirred under reflux for 1.5 hours under a nitrogen atmosphere. The reaction mixture was then evaporated to dryness under vacuum, and the residue was dissolved in 200 ml. of water and washed with 300 ml. of diethyl ether. The water layer was degassed under vacuum, and then nitrogen was bubbled through it to remove all traces of ether. The mixture was then acidified with 1 N hydrochloric acid, and then made basic with excess sodium bicarbonate. The precipitate was collected by filtration and washed with cold water to obtain 2.4 g. of crude product. It was purified on a 2×30 cm. column of silica gel, eluting first with 700 ml. of 55 methanol in chloroform, followed by 1 liter of 10% methanol in chloroform. The impurities came off first, and the product-containing fractions were combined and evaporated under vacuum to obtain 1.78 g. of yellow oil. The oil was dissolved in 6 ml of acetone, seeded and chilled in a freezer to obtain 1.2 g. of purified product, m.p. 143°–147° C. The identity of the product was confirmed as follows:

nmr spectrum (100 mHz in dmso-$d_6$) δ 1.20–1.65(6H, m. N($CH_2CH_2$)$_2CH_2$); 2.30–2.45 (4H, m, N($CH_2CH_2$)$_2$ $CH_2$); 2.60 (2H, t, J=6 Hz, OC$H_2CH_2$N); 4.06(2H, t, J=6 Hz, OC$H_2CH_2$N); 6.68(2H, d, J=9H, aromatic o to OH); 6.85(1H, q, $J_{H4-H5}$=9Hz, $J_{H5-H7}$=2 Hz, H5 of benzothiophene ring); 6.90(2H, d, J=9 Hz, aromatic o to OC$H_2CH_2$N); 7.18 (2H, d, J=9 Hz, aromatic m to OH); 7.25 (1H, d, J=9z, H4 of benzothiopene ring); 7.66 (2H, d, J=9 Hz, aromatic o to CO); 9.72(2H, broad s, OH). Ultraviolet spectrum in ethanol; $\lambda_{max}(\epsilon)$: 290 nm. (34,000). Electron impact mass spectrum $M_t$ at m/e 473.

PREPARATION 2

6-Hydroxy-2-(4-Hydroxyphenyl)-3[-4-(2-piperidinoethoxy)benzoyl]benzo[b]thiophene A 3.6 g. portion of 6-methanesulfonyloxy-2-(4-methanesulfonyloxyphenyl)-3-[4-(2-piperidinoethoxy)-benzoyl]benzo[b]thiophene was dissolved in 100 ml. of tetrahydrofuran and 40 ml. of methanol, and 10 ml. of 5 N sodium hydroxide was added. The mixture was stirred for 16 hours at ambient temperature, and was then worked up by the procedure of Example 1 above to obtain 3.5 g of a yellow solid. The impure product was purified by column chromatography on silica gel, eluting with a gradient solvent from 5% methanol in chloroform to 30% methanol in chloroform. The product-containing fractions were evaporated to obtain 1.85 g. of oily product, which was recrystallized from acetone to obtain 1.25 g of purified product, m.p. 141°–144° C.

PREPARATION 3

6-Hydroxy-2-(4-Hydroxyphenyl)-3[4-(2-piperidinoethoxy)benzoyl]benzo[b]thiophene, Hydrochloride Under a nitrogen blanket, a mixture of 3 g. of 4-(2-piperidinoethoxy)benzoic acid, hydrochloride, 2 drops of dimethylformamide, 2.5 ml. of thionyl chloride and 40 ml. of chlorobenzene was heated at 70°–75° C. for about one hour. The excess thionyl chloride and 15–20 ml. of solvent were then distilled off. The remaining suspension was cooled to ambient temperature, and to it were added 100 ml. of dichloromethane, 2.7 g. of 6-methoxy-2-(4-methoxyphenyl)benzo[b]thiophene and 10 g. of aluminum chloride. The solution was stirred for about one hour, 7.5 ml. of ethanethiol was added, and the mixture was stirred for 45 minutes more. Then 40 ml. of tetrahydrofuran was added, followed by 15 ml. of 20% hydrochloric acid, with an exotherm to reflux. Fifty ml. of water and 25 ml. of saturated aqueous sodium chloride were added. The mixture was stirred and allowed to cool to ambient temperature. The precipitate was collected by filtration and washed successively with 30 ml. of water, 40 ml of 25% aqueous tetrahydrofuran, and 35 ml. of water. The solids were then dried at 40° C. under vacuum to obtain 5.05 g. of product, which was identified by nmr.

δ 1.7(6H, m, N(CH$_2$CH$_2$)$_2$CH$_2$); 2.6–3.1(2H, m, NCH2); 3.5–4.1 (4H, m, NCH$_2$); 4.4(2H, m, OCH$_2$); 6.6–7.4(9H, m, aromatic); 7.7(2H, d, aromatic o to CO); 9.8(2H, m, OH).

EXAMPLE 1

6-TBDMS-RALOXIFENE AND 4'-TBDMS-RALOXIFENE

2H), 2.79 (t, 5.6 Hz, 2H), 2.56 (m, 4H), 1.67 (m, 4H), 1.46 (m, 2H), 0.92 (s, 9H), 0.12 (s, 6H); IR (CHCl$_3$) 2938, 2860, 1643, 1600, 1572, 1535, 1508, 1496, 1469, 1421, 1345, 1304, 1258, 1167, 1038, 907, 841, 808 cm$^{-1}$; elemental analysis calc.: 69.47% C, 7.03% H, 2.38% N. found: 69.19% C, 6.98% H, 2.57% N: FD/MS 587 6-TBDMS-raloxifene : $^1$H NMR (CDCl$_3$ (300 MHz) d 7.60 (d, J=8.9 Hz, 2H), 7.62 (s, 1H), 7.27 (d, J=2.3 Hz, 1H), 7.15 (d, J=8.4 Hz, 2H), 6.89 (dd, J=8.7, 2.2 Hz, 1H), 6.64 (d, J=7.0 Hz, 2H), 6.58 (d, J=6.9 Hz, 2H), 4.08 (t, J=5.6 Hz, 2H), 2.77 (t, J=5.6 Hz, 2H), 2.56 (m, 4H), 1.64 (m, 4H), 1.47 (m, 2H), 1.00 (s, 9H), 0.23 (s, 6H). IR 2938, 2860, 1640, 1599, 1573, 1536, 1508, 1467, 1353, 1307, 1257, 1167, 1073, 1041, 944, 840, 829, 815 cm-$^1$; elemental analysis calc.: 69.47% C, 7.03% H, 2.38% N. found: 69.28% C, 7.30% H, 2.50% N; FD/MS-587

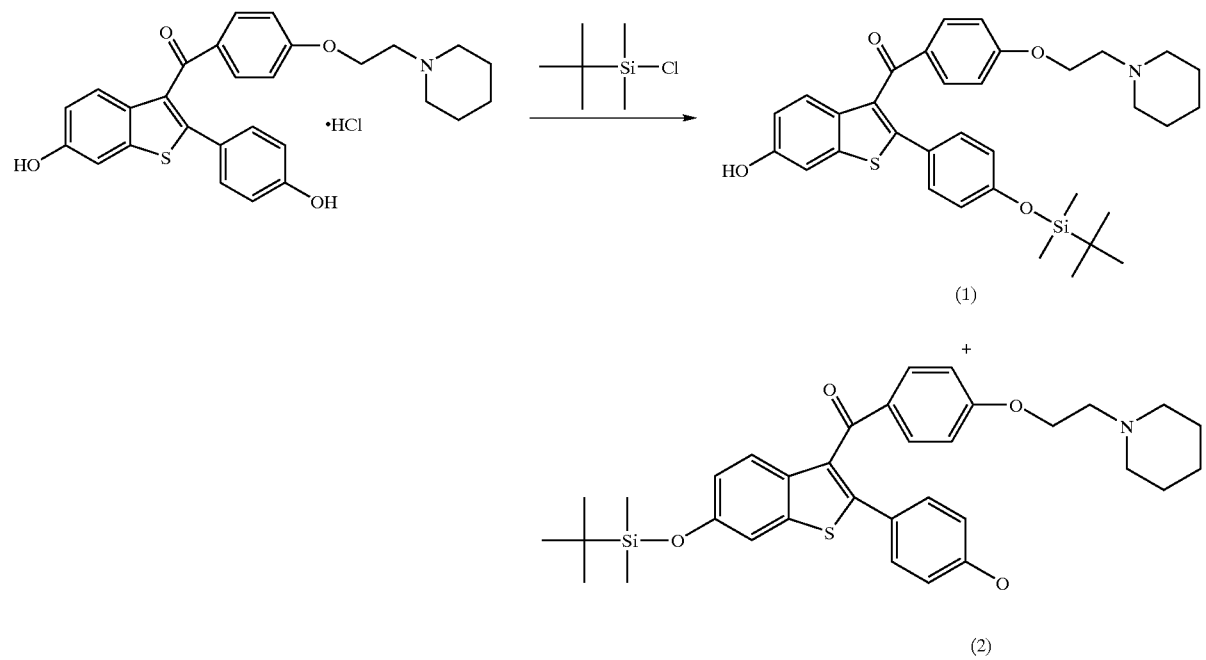

A solution of raloxifene (10.0 g, 21.1 mmol) and dimethylaminopyridine (6.0 g, 49.1 mmol) in 6:1 THF/DMF (700 ml) was stirred at room temperature for 1 hour. The solution was then cooled to 0° C. and t-butyldimethylsilyl chloride (2.9 g, 19.3 mmol) was added slowly. The cooling bath was removed and the reaction mixture was warmed to room temperature. After 72 hours, the mixture was washed with saturated aqueous ammonium chloride, water, and brine. The organic extract was dried over sodium sulfate, then was filtered and concentrated. The crude product was triturated with CH$_2$Cl$_2$ and the resulting mixture allowed to stand at room temperature for 3 hours then filtered to remove unreacted starting material. To the filtrate was added silica (500 g) and the slurry carefully concentrated. This material was purified by flash chromatography (silica gel, chloroform/methanol gradient) to give 5.1 g of 1 (41%) and 4.8 g of 2 (38%) both as yellow crystalline solids. 4'-TBDMS-raloxifene: $^1$H NMR (CDCl$_3$ (300 MHz) d 7.63 (d, J=8.9, 2H), 7.44 (d, J=8.8, 1H), 7.20 (d, J=8.6 Hz, 2H), 7.17 (d, J=2.2 Hz, 1H), 6.77 (d, J=8.7, 2.2 Hz, 1H), 6.66 (d, J=8.5 Hz, 2H), 6.55 (d, J=8.9 Hz, 2H), 4.07 (t, J=5.7 Hz,

EXAMPLE 2

METHYL-1-(4'-TBDMS-6-HYDROXY-RALOXIFENE)-

2,3,4-TRI-O-ACETYL-β-D-GLUCOPYRANOSIDE URONATE

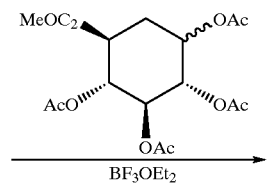

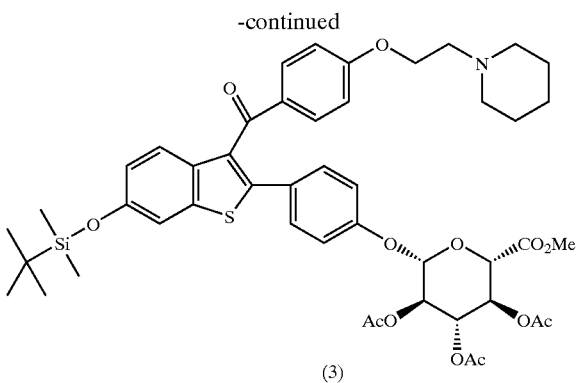

(3)

To 2 (2.0 g, 3.4 mmol) stirring in dry CH$_2$Cl$_2$ (100 ml) at room temperature was added methyl-1,2,3,4-tetra-O-acetyl-D-glucopyranuronate (1.3 g, 3.4 mmol) followed by 4A molecular sieves (1.2 g). After 10 min at room temperature, boron trifluoride etherate (2.5 ml, 20.4 mmol) was added dropwise via syringe. After 18 hours at room temperature, the dark red solution was poured into a separatory funnel containing saturated aq. NaHCO$_3$ and CH$_2$Cl$_2$. The organic layer was extracted and washed with water, brine then dried (sodium sulfate). The crude residue was purified by flash chromatography (silica gel, CHCl$_3$ to 2% MeOH/CHCl$_3$ gradient) to give 1.08 g (35%) of 3 as a yellow foam $^1$H NMR (300 MHz, DMSO-d$_6$) d 7.66 (d, J=8.8 Hz, 2H), 7.55 (d, J=2.1 Hz, 1H), 7.30 (m, 3H), 6.91 (m, 5H), 5.61 (d, J=7.7 Hz, 1H), 5.38 (m, 1H), 5.01 (m, 2H), 4.64 (d, J=9.9 Hz, 1H), 4.06 (t, 2H), 3.59 (s, 3H), 2.60 (m, 2H), 2.37 (m, 4H), 1.98 (s, 3H), 1.96 (s, 6H), 1.43 (m, 4H), 1.33 (m, 2H), 0.95 (s, 9H), 0.20 (s, 6H); IR (CHCl$_3$) 2938, 2859, 1758, 1646, 1598, 1573, 1534, 1508, 1497, 1467, 1374, 1306, 1256, 1167, 1073, 1040, 946, 840 cm$^{-1}$; elemental analysis: calc. 62.44% C, 6.36% H, 1.55% N. found: 62.66% C, 6.63% H, 1.50% N: FD/MS-905.

EXAMPLE 3

METHYL-1-(6-TBDMS-4'HYDROXY-RALOXIFENE)-2,3,4-O-TRIACETYL-β-D-GLUCOPYRANOSIDE URONATE

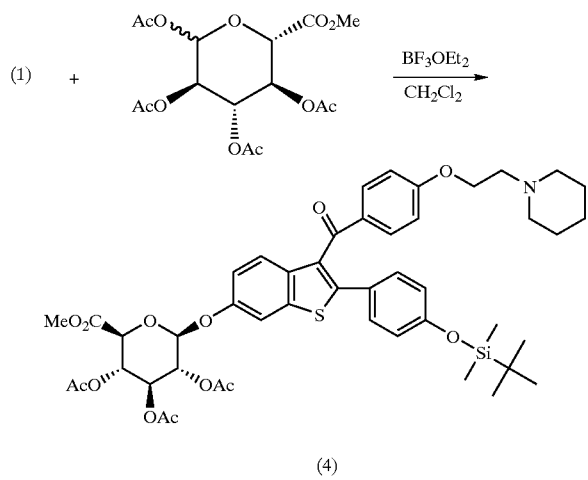

To 1 (0.5 g, 0.85 mmol) stirring at room temperature in dry CH$_2$Cl$_2$ (10 ml) was added methyl-1,2,3,4-O-tetraacetyl-D-glucopyranuronate (0.31 g, 0.85 mmol) followed by 4A molecular sieves (0.33 g). After 10 min. at room temperature, boron trifluoride etherate (0.60 ml, 5.10 mmol) was added dropwise via syringe. After 18 hours at room temperature, the reaction mixture poured into a separatory funnel containing saturated aq. NaHCO$_3$ and CH$_2$Cl$_2$. The organic layer was quickly extracted and washed with water, brine and dried (sodium sulfate). Filtration and concentration gave a crude solid which was purified by flash chromatography (silica gel, CHCl$_3$ to 2% MeOH/CHCl$_3$ gradient) to give 0.18 g of 4 (23%) as a yellow foam. $^1$H NMR (300 MHz, DMSO-d$_6$) d 7.76 (s, 1H), 7.58 (d, J=8.7 Hz, 2H), 7.47 (d, J=8.9 Hz, 1H), 7.23 (d, J=8.5 Hz, 2H), 7.05 (d, J=8.8 Hz, 1H), 6.84 (d, J=8.8 Hz, 2H), 6.74 (d, J=8.5 Hz, 2H), 5.70 (d, J=7.9 Hz, 1H), 5.46 (dd, J=9.5, 9.6 Hz, 1H), 5.08 (m, 2H), 4.70 (d, J=10.0 Hz, 1H), 4.01 (t, J=5.4 Hz, 2H), 3.62 (s, 3H), 2.58 (m, 2H), 2.36 (m, 4H), 2.01 (s, 3H), 1.99 (s, 3H), 1.98 (s, 3H), 1.43 (m, 4H), 1.33 (m, 2H), 0.86 (s, 9H), 0.085 (s, 6H); IR (CHCl$_3$) 2938, 2859, 1759, 1600, 1572, 1534, 1508, 1497, 1468, 1374, 1255, 1241, 1167, 1073, 1045, 908, 841 cm$^{-1}$; Elemental analysis, calc.: 62.44% C, 6.35% H, 1.55% N. found: 62.68% C, 6.47% H, 1.61% N; FD/MS-905.

EXAMPLE 4

6-RALOXIFENE-β-D-GLUCOPYRANOSIDE (4) 1. LiOH/dioxane
2. tetrabutyl ammonium fluoride

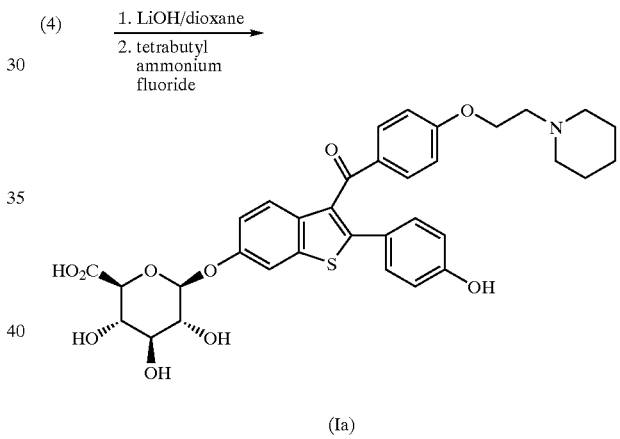

(Ia)

To 4 (0.50 g, 0.55 mmol) stirring at room temperature in dioxane (100 ml) was added LIOH monohydrate (0.14 g, 3.33 mmol). The reaction mixture was heated to 60° C. for approximately 96 hours. The solution was cooled to room temperature and tetrabutylammonium flouride (1.1 ml of a 1M solution in THF) was added. The resulting orange solution was stirred at room temperature for 5 minutes then concentrated. Ammonium acetate (30 ml, 0.05M, pH=4.0) was added to the crude product followed by addition of sufficient methanol to provide a homogeneous solution. The mixture was purified on a Waters 4000 reverse phase HPLC with two 20×100 cm Novapak cartridges (wavelength=290 nm, flow rate=40 ml/min, collect approx. 20 ml fractions, isocratic conditions at 80% 0.05M ammonium acetate (pH= 4.0), 20% MeOH). This purification procedure was repeated three times. The product was concentrated and desalted using standard techniques on an HP-20 resin. Concentration yielded 46 mg of Ia (13%) as a crystalline yellow solid : $^1$H NMR (500 MHz, DMSO-d$_6$) d 9.86 (bs, 0.6H), 7.70 (s, 1H), 7.66 (d, 2H), 7.31 (d, 1H), 7.21 (d, 2H), 7.06 (d, 1H), 6.92 (d, 2H), 6.70 (d, 2H), 5.25 (bs, 0.8H), 4.97 (bs, 0.5H), 4.93 (d, 1H, J=7.4), 4.08 (t, 2H), 3.42 (d, J=10.1 Hz, 1H), 3.24 (m, 2H), 3.12 (dd, J=10.0, 8.3 Hz, 1H), 2.61 (t, 2H), 2.39 (m, 4H), 1.46 (m, 4H), 1.36 (m, 2H); High resolution FAB/MS, calc. 650.2060, found 650.2036.

EXAMPLE 5

4'-RALOXIFENE-β-D-GLUCOPYRANOSIDE

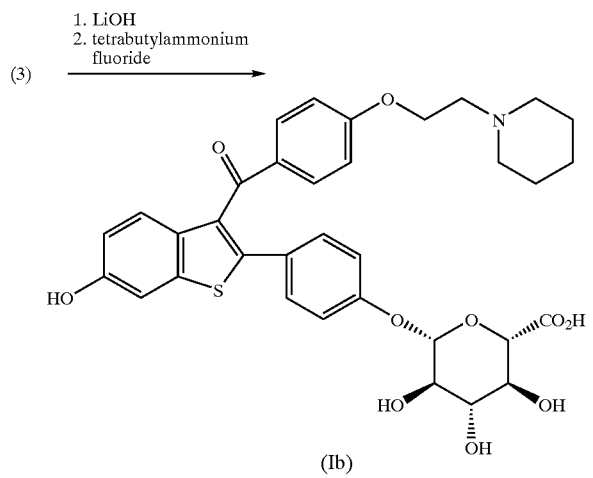

To 3 (0.50 g, 0.55 mmol) stirring at room temperature in dioxane (100 mL) was added LiOH monohydrate (0.14 g, 3.32 mmol). The reaction mixture was heated to 60° C. for approximately 96 hrs. The solution was cooled to room temperature and tetrabutylammonium fluoride (1.1 ml of a 1M solution in THF) was added. The resulting orange solution was stirred at room temperature for 5 minutes then concentrated. Ammonium acetate (30 ml, 0.05M, pH=4.0) was added to the crude product followed by addition of sufficient acetonitrile to provide a homogeneous solution. The mixture was purified on a Waters 4000 reverse phase HPLC with two 20×100 cm Novapak cartridges (wavelength=290 nm, flow rate=40 ml/min , collect approx. 20 ml fractions). Fractions containing the desired product were combined, concentrated, and desalted by adding water. This was filtered and rinsed with water. The product was then eluted with methanol. Concentration gave 240 mg (67%) of pure product (Ib) as a yellow solid: $^1$H NMR (500 MHz, DMSO-$d_6$) d 9.86 (bs, 1H), 7.63 (d, 2H), 7.43 (d, 1H), 7.37 (s, 1H), 7.23 (d, 2H), 6.89 (d, 3H), 6.85 (d, 2H), 5.34 (bs, 1H), 5.14 (bs, 1H), 5.00 (d, J=7.8 Hz, 1H), 4.16 (m, 2H), 3.67 (d, J=9.2 Hz, 1H), 3.26 (m, 2H), 3.19 (m, 1H), 2.94 (bm, 2H), 2.74 (bm, 4H), 1.61 (m, 4H), 1.43 (m, 2H); high resolution FAB/MS 650.20 (calc. 650.20).

Test Procedure 1

A post-menopausal model was used in which effects of different treatments upon circulating lipids were determined.

Seventy-five day old female Sprague Dawley rats (weight range of 200 to 225 g) were obtained from Charles River Laboratories (Portage, Mich.). The animals were either bilaterally ovariectomized (OVX) or exposed to a sham surgical procedure at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at 22.2°±1.7° C. with a minimum relative humidity of 40%. The photoperiod in the room was 12 hours light and 12 hours dark.

Dosina Regimen/Tissue Collection. After a one week acclimation period (therefore, two weeks post-OVX) daily dosing with test compound was initiated. All compounds were administered subcutaneously at the dosages listed. Animals were dosed daily for 4 days. Following the dosing regimen animals were weighed and anesthetized with a ketamine: xylazine (2:1, [V:V] mixture and a blood sample was collected by cardiac puncture. The animals were then sacrificed by asphyxiation with $CO_2$ and the uterus was removed through a midline incision and a wet weight was determined.

Cholesterol Analysis. Blood samples were allowed to clot at room temperature for 2 hrs, and serum was obtained following centrifugation for 10 min at 3000 rpm. Serum cholesterol was determined using a Boehringer Mannheim Diagnostics high performance cholesterol assay. Briefly the cholesterol was oxidized to cholest-4-en-3-one and hydrogen peroxide. The hydrogen peroxide was then reacted with phenol and 4-aminophenazone in the presence of peroxidase to produce a p-quinone imine dye, which was read spectrophotometrically at 500 nm. Cholesterol concentration was then calculated against a standard curve. The entire assay was automated using a Biomek Automated workstation.

Uterine Eosinophil Peroxidase (EPO) Assay. The presence of eosinophils in the uterus is an indication of estrogenic activity of a compound. To maintain EPO activity, uteri were kept at 4° C. until time of enzymatic analysis. The uteri were then homogenized in 50 volumes of 50 mM Tris buffer (pH-8.0) containing 0.005% Triton X-100. Upon addition of 0.01% hydrogen peroxide and 10 mM o-phenylenediamine (final concentrations) in Tris buffer, increase in absorbance was monitored for one minute at 450 nm. The maximal velocity of a 15 second interval was determined over the initial linear portion of the reaction curve.

The results of treatments are presented below. In summary, ovariectomy of the rats caused an increase in serum cholesterol as compared to intact vehicle treated controls.

In these studies, the compounds caused a serum cholesterol decrease in a dose dependent manner; however, only minimal increase of uterine weight and little or no stimulation of EPO activity over the ovariectomized controls was present in treated animals.

| Compound | Dose (mg/kg) | % Decrease of Serum Cholesterol[a] | % Uterine Wt. gain[b] | EPO Activity (n OD/min)[c] |
|---|---|---|---|---|
| Ia | 0.013 | 21.7 | −21.3 | 2.0 |
|  | 0.13 | 43.8 | 14.2 | 2.3 |
|  | 1.3 | 44.5 | 24.1 | 3.5 |
| Ib | 0.013 | 13.6 | −7.7 | 3.2 |
|  | 0.13 | 21.9 | 14.5 | 3.1 |
|  | 1.3 | 56.8 | 36.1 | 4.4 |

[a]Percent decrease of serum cholesterol equals (serum cholesterol of treated OVX animals minus serum cholesterol of OVX animals) divided by (serum cholesterol of control OVX animals) multiplied by 100.
[b]Percent uterine weight gain equals (uterine weight of treated OVX animals minus uterine weight of control OVX animals) divided by (uterine weight of control OVX animals) multiplied by 100.
[c]$V_{max}$ for eosinophil peroxidase activity.

Test Procedure 2

To mimic the in vivo environment for inhibition of bone loss, a rat marrow culture technique which acts as an osteoclast differentiation model (in the absence of 1,25 vitamin D and in the presence of bone), was used. It has been found that marrow cells from neonatal rat long bones will differentiate and resorb significant amounts of bone over a 4-day period in the presence of 0.1 μg/ml IL-6. Specifically, marrow cells from 2-day old neonates were cultured on bone slices at a density of $2 \times 10^5/cm^2$ in 199 media (Gibco) with 20% heat inactivated fetal bovine serum (Gibco) and 0.1 μg/ml IL-6 for 4 days. After incubation, bone slices were devitalized, fixed, dehydrated, and stained with 1% toluidine blue in 1% sodium borate for 1 min; and resorption lacunae were quantitated by reflected polarized light microscopy. The compounds inhibited this cytokine stimulated resorption and both compounds had $IC_{50}$s of about 10 mM.

What is claimed is:

1. A method of inhibiting postmenopausal osteoporosis comprising administering a compound of formulae

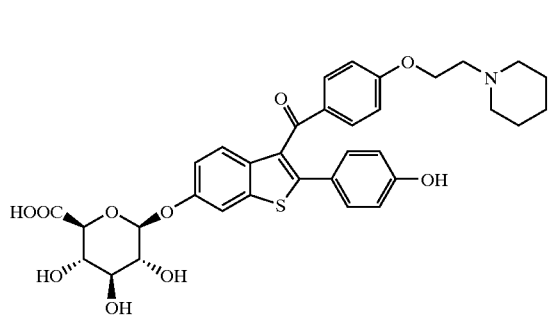

(Ia)

or

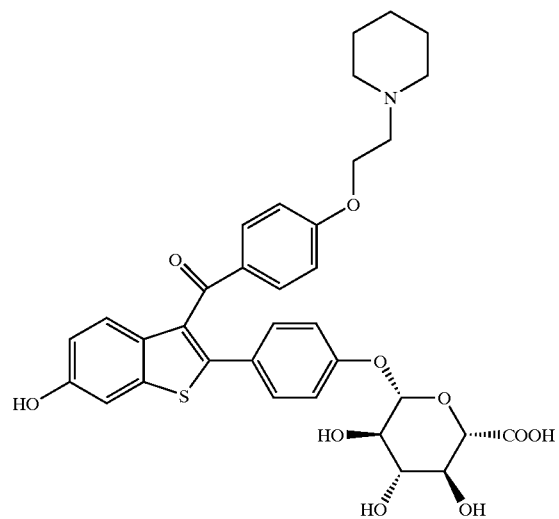

(Ib)

or a pharmaceutically acceptable salt or solvate thereof to a woman in need thereof.

* * * * *